United States Patent
Southard et al.

(10) Patent No.: US 10,010,073 B2
(45) Date of Patent: Jul. 3, 2018

(54) PERSISTENT SANITIZER COMPOSITION BASED ON CYCLOMETHICONE

(71) Applicant: Relevo, Inc., Carmel, IN (US)

(72) Inventors: Jeffrey L. Southard, Olathe, KS (US); Brian K. Southard, Carmel, IN (US)

(73) Assignee: Relevo, Inc., Carmel, IN (US)

( * ) Notice: Subject to any disclaimer, the term of this patent is extended or adjusted under 35 U.S.C. 154(b) by 0 days.

(21) Appl. No.: 15/125,144

(22) PCT Filed: Mar. 12, 2015

(86) PCT No.: PCT/US2015/020145
§ 371 (c)(1),
(2) Date: Sep. 10, 2016

(87) PCT Pub. No.: WO2015/138705
PCT Pub. Date: Sep. 17, 2015

(65) Prior Publication Data
US 2016/0374336 A1    Dec. 29, 2016

Related U.S. Application Data

(60) Provisional application No. 61/952,503, filed on Mar. 13, 2014.

(51) Int. Cl.
| | | |
|---|---|---|
| C11D 1/62 | (2006.01) | |
| C11D 3/48 | (2006.01) | |
| C11D 7/50 | (2006.01) | |
| C11D 9/36 | (2006.01) | |
| C11D 3/50 | (2006.01) | |
| A01N 33/12 | (2006.01) | |
| B05B 11/00 | (2006.01) | |
| B65D 83/54 | (2006.01) | |
| B65D 83/62 | (2006.01) | |

(52) U.S. Cl.
CPC .............. *A01N 33/12* (2013.01); *B05B 11/30* (2013.01); *B65D 83/54* (2013.01); *B65D 83/62* (2013.01)

(58) Field of Classification Search
CPC .... C11D 1/62; C11D 3/48; C11D 3/50; C11D 3/162; C11D 7/50; C11D 7/5077; C11D 7/5095; C11D 9/36; C11D 17/0043
See application file for complete search history.

(56) References Cited

U.S. PATENT DOCUMENTS

| | | | |
|---|---|---|---|
| 3,118,572 A | 1/1964 | Harding | |
| 5,217,641 A * | 6/1993 | Herstein | A61K 8/37 510/136 |
| 6,248,343 B1 * | 6/2001 | Jampani | A01N 31/02 424/401 |
| 6,423,329 B1 | 7/2002 | Sine | |
| 6,617,294 B2 * | 9/2003 | Narula | A01N 31/02 510/138 |
| 2003/0139307 A1 * | 7/2003 | Narula | A01N 31/02 510/138 |
| 2005/0132508 A1 * | 6/2005 | Overdevest | D06L 1/12 8/412 |
| 2009/0038083 A1 | 2/2009 | Roselle | |
| 2014/0199249 A1 * | 7/2014 | Cooper | A01N 25/02 424/59 |
| 2014/0343158 A1 * | 11/2014 | Fusco | A61K 31/045 514/643 |

FOREIGN PATENT DOCUMENTS

| | | |
|---|---|---|
| WO | WO 2010/063988 A1 | 6/2010 |
| WO | WO 2013/067150 A2 | 5/2013 |

OTHER PUBLICATIONS

International Search Report dated Jun. 12, 2015, for PCT/US2015/020145.

* cited by examiner

*Primary Examiner* — Charles Boyer
(74) *Attorney, Agent, or Firm* — Clayton, McKay & Bailey, PC

(57) ABSTRACT

A waterless and essentially alcohol-free sanitizer composition or aerosolized hand sanitizing composition containing a quaternary ammonium salt such as benzalkonium chloride to kill germs and bacteria, a volatile carrier such as cyclomethicone, additional moisturizers, and optionally fragrance or other additives.

25 Claims, No Drawings

PERSISTENT SANITIZER COMPOSITION BASED ON CYCLOMETHICONE

CROSS REFERENCE TO RELATED APPLICATIONS

This application claims the benefit of priority to U.S. Provisional Patent Application Ser. No. 61/952,530, filed Mar. 13, 2014, the disclosure of which is incorporated herein by reference in its entirety.

FIELD OF INVENTION

This invention relates generally to a formula for an aerosolized sanitizing composition that is water and functionally alcohol free.

BACKGROUND OF THE INVENTION

Sanitizing substances used as a disinfectant are intended to reduce the risk of exposure to and the spread of germs encountered in day-to-day activities.

Although the use of sanitizing hand gels and foams is well known, a need exists for an aerosolized formulation that will persistently kill a broad spectrum of germs, provide superior coverage, and dry quickly without dehydrating the skin. However, many such quick drying gels and foams have compositions that lack germicidal persistence once the anti-microbial agent has evaporated, leave an undesirable sticky residue and will dehydrate the skin with frequent use. Accordingly, the need exists for an aerosolized composition with persistent germicidal activity, and is functionally free of water and alcohol. Furthermore the composition is compliant with the requirements necessary for safe and effective use in healthcare facilities and public schools, and containing FDA GRAS (Generally Regarded as Safe) listed components.

The World Health Organization (WHO) and the Center for Disease Control (CDC) recommend "persistent" antiseptics for hand sanitizers. Persistent activity is defined as the prolonged or extended antimicrobial activity that prevents or inhibits the proliferation or survival of microorganisms after application of the product. The popular alcohol based hand sanitizers while quick, effective and inexpensive are not persistent sanitizing agents and must be reapplied frequently to maintain antiseptic criteria.

SCHEME OF THE INVENTION

The purpose of the invention is to formulate a waterless and functionally alcohol-free or completely alcohol-free sanitizer that meets the persistent activity recommended by WHO and CDC. This sanitizer is useful for sanitizing hands and will provide the benefits and qualities to which users of alcohol based hand sanitizers are accustom. It is a further purpose of the invention to develop a hand sanitizer that incorporates GRAS listed components that evaporate quickly, have residual germicidal activity, and limit dehydration of the skin.

Accordingly, the invention provides an aerosolized persistent germicidal formula for a sanitizing substance, which is used in lieu of or in conjunction with traditional hand-washing. The invention also provides a persistent germicidal solution having broad-spectrum germicidal effect. The invention further provides a method of promoting hygiene. The above noted and other purposes of the present invention will become readily apparent upon further review of the following specification and claims.

SUMMARY OF INVENTION

The invention is directed generally to an antimicrobial formula for a persistent sanitizing composition that effectively kills 99.9% of germs, is applied as an aerosol, and leaves the user's hands moist and smooth without any sticky residue.

An aspect of the invention is a water free and essentially or completely alcohol free sanitizer composition suitable for use on the hands, comprising a germicidal component of up to about 1% by weight, preferably about 0.1% (4×) to about 0.8% (6×), more preferably about 0.1 to about 0.2% of the total composition by weight percentage. The germicidal component is the active pharmaceutical ingredient (API) such as a germicidal quaternary ammonium salt (hereinafter a QUAT). Especially preferably, the QUAT may be benzalkonium chloride (BAK). The QUAT is dissolved in a minimal amount of solvent such as the carrier (cyclomethicone), optional water or optional alcohol. When cyclomethicone is used alone as the carrier and solvent for the composition, it is completely free of alcohol and water.[1] When water and/or alcohol are used as solvent, the cyclomethicone is also present such that the optional water and/or optional alcohol are present in an amount of up to about 0.5% by weight, preferably up to about 0.3% of the total composition by weight percentage, more preferably up to about 0.15% by weight, most preferably up to about 0.13% by weight. The water may be deionized, distilled or may contain minerals commonly found in potable water. The alcohol may be ethyl alcohol (EA) or isopropyl alcohol (IPA). The alcohol preferably is essentially anhydrous but may contain and/or absorb residual water. More preferably the alcohol is 200 proof.

[1] The term "completely free" in this context means that water and alcohol have not been intentionally added, however residual water and/or alcohol carried with other ingredients or absorbed from the atmosphere may be present. This presence is included within the phrase (completely free).

The composition further may comprise beneficial, essential oils at concentrations of up to about 10%, preferably about 4% to about 10%. Stabilizing agents such as antioxidant and preservatives at appropriate small concentrations such as up to about 1% may also be present. A preferred antioxidant is Tocopheryl Acetate (vitamin E) at a concentration of about 0.25% to about 0.75%. A cooling agent such as menthol or a menthol deriviative such as Frescolat x at an appropriate concentration such as up to about 1% by weight may also be present.

The liquid carrier for homogeneously mixing and solvating the other components of the composition is cyclomethicone. This carrier is present at a concentration by weight of up to 98% by weight, preferably from about 85% to about 98% by weight of the total composition. Optionally, fragrance may be added at a concentration of about 0.5% to about 1.0% or as needed based on strength of fragrance.

The present invention includes a method for preparing an aerosolized persistent sanitizer composition, comprising the steps of combining at least a portion of the solvent and QUAT to form a base API mixture. The base API mixture is ready to receive the addition of essential oils, Tocopheryl acetate (TA), and fragrance. The oils, TA and fragrance are added to the base API mixture, to form a functional mixture that ensures the rapid, uniform dissolution into the carrier cyclomethicone. This method can also include the further steps of adding one or more stabilizing agents from a group of anti-oxidants and preservatives and adding an optional cooling agent.

DETAILED DESCRIPTION OF THE INVENTION

Although the use of sanitizing hand gels is well known, a need exists for a formulation that is persistent and will effectively kill germs, dry quickly, leave no sticky residue, or excessively dry the skin. Most hand sanitizers with high alcohol content will excessively dry the skin. As a result, it is common to restrict the alcohol content in hand sanitizers to approximately 62 percent. Decreasing the alcohol content has the unwanted effect of decreasing the composition's potency for killing germs and bacteria.

The present invention is directed to a composition for a persistent sanitizer with an bioactive ingredient that is safe and effective in killing germs, dries quickly, does not leave a sticky residue, and does not excessively dry the skin. In various embodiments, the present invention is directed to a composition and method of making a hand sanitizing composition that persistently kills germs and is gentle to the skin. Another feature of this formula is that it is delivered by aerosol and will not leave a sticky residue or feeling on the skin after use. This invention achieves all these functions with a single composition.

The invention also includes a method of preparing the composition.

One embodiment of the present invention has been shown to kill 99.9% of germs in seconds of administration to common bacterial (germ) cultures. It is a persistent sanitizing composition that is essentially water-free and/or alcohol-free and preferably is completely water free and alcohol free. It is intended for use in conjunction with or in place of traditionally used soap and water or germicidal towelettes such as described in U.S. Pat. No 5,753,246, which is hereby incorporated by reference.

Specifically in a preferred embodiment the sanitizing composition is comprised of a bioactive ingredient with recognized persistent activity to kill germs and bacteria, cyclomethicone, essential oils and anti-oxidants to moisturize and protect skin, stabilizing components from the group of anti-oxidants and preservatives, a suitable aerosol propellant, and optional fragrance and optional cooling agent.

In the preferred embodiment the sanitizing composition is comprised of the bioactive ingredient which is a quaternary ammonium salt (QUAT) having anti-microbial and anti-viral properties (anti-germ properties) to kill germs and bacteria, a solvent for dissolution of API, cyclomethicone, one or more essential oils, anti-oxidants, a suitable aerosol propellant, and optional fragrance and optional cooling agent.

In embodiments of the invention, the QUAT acting as the bioactive ingredient is selected from the group consisting of benzalkonium chloride, benzethonium chloride, methylbenzethonium chloride, cetalkonium chloride, cetylpyridinium chloride, cetrimonium, cetrimide, dofanium chloride, tetraethylammonium bromide, domiphen bromide and any combination thereof. These QUATs have known anti-bacterial, anti-microbial and anti-viral properties so that they kill microbes, germs, viruses and bacteria. The preferred QUAT is benzalkonium chloride, benzethonium chloride or cetyl pyridinium chloride. The especially preferred QUAT is benzalkonium chloride. The concentration of QUAT in the composition of the invention ranges up to about 1% by weight, preferably from 0.5% to 0.8% by weight, more preferably from about 0.13% to about 0.6% by weight, most preferably 0.10% top 0.15% by weight with the most preferred individual percentage being about 0.13% by weight.

In embodiments of the invention, when the solvent for the QUAT is other than cyclodimethicone, the solvent is optionally present at a minimal concentration, preferably enough only to dissolve the QUAT. Most preferably, however, the solvent is cyclodimethicone so that the other liquids that could serve as solvent, such as water and/or alcohol, are absent.

When present in the composition of the invention as a solvent for the QUAT, the alcohol is may be a version that is water-free so that the hand sanitizer composition will be essentially water free. Preferably, the alcohol used as a starting ingredient is anhydrous, preferably may be denatured and more preferably may be 200 proof. The alcohol may be ethyl alcohol or isopropyl alcohol. The minimal concentration of alcohol in the sanitizer composition means that the alcohol is functionally irrelevant. The concentration of alcohol in the composition ranges up to about 1.5% by weight preferably up to about 1% by weight. Because alcohol is capable of absorbing water from the atmosphere, some residual water may be present in the hand sanitizing composition in combination with optional alcohol.

When embodiments of the invention are completely alcohol free, they optionally may contain a minimal amount water as a solvent for the QUAT. The water concentration may be on the order of about 0.05% to about 0.2% by weight, preferably about 0.1% to about 0.15% by weight, more preferably about 0.13% by weight. The water may be deionized, distilled or may contain minute traces of minerals commonly found in potable water.

When alcohol as a solvent is present in the composition of the invention, its minimal concentration enables the non-drying property of the hand sanitizer composition. When water as a solvent is present in the composition of the invention, its minimal concentration avoids leaching of natural oils and components from the skin. As a result, the hand sanitizer composition of the invention will not dry the skin as known alcohol based sanitizers are capable of. Thus, all solvent variations of the persistent hand sanitizer (composition) of the invention avoid the skin drying property associated with alcohol based skin sanitizers.

Cyclomethicone is the carrier component of the sanitizing composition and may optionally also act as a solvent for the QUAT and other components of the composition. It is an odorless volatile liquid in which the other components of the sanitizing composition are soluble. Upon application to the skin, cyclomethicone expeditiously evaporates allowing the QUAT, oils, stabilizer and other optional ingredients to remain and provide residual germicidal activation with little or no skin drying effect. The concentration of cyclomethicone in the composition ranges from 60% up to about 98% by weight, and this percentage includes all integer numbers between these two numbers of the range, preferably from about 85% to about 98% by weight, more preferably from about 90% by weight to about 98% by weight.

In an embodiment, the sanitizer composition is comprised of one or more QUATs, cyclomethicone as a carrier and solvent for dissolution of the QUAT, one or more essential oils, anti-oxidants, a suitable aerosol propellant, and optional fragrance and optional cooling agent.

In another embodiment, the sanitizer composition is comprised of one or more QUATs, a minimal concentration of solvent for dissolution of QUAT, cyclomethicone, one or more essential oils, anti-oxidants, a suitable aerosol propellant, and optional fragrance and optional cooling agent.

In another embodiment the sanitizer composition is comprised of one or more QUATs, a minimal concentration of anhydrous isopropyl alcohol or absolute ethanol, cyclomethicone, essential oils and anti-oxidants to moisturize and protect skin, stabilizing components, a suitable aerosol propellant, and optional fragrance and optional cooling agent.

In another embodiment the sanitizer composition is comprised of one or more QUATs, a minimal concentration of water, cyclomethicone, essential oils and anti-oxidants to moisturize and protect skin, stabilizing components, a suitable aerosol propellant, and optional fragrance and optional cooling agent.

In another embodiment the sanitizer composition is comprised of one or more QUATs and Triclosan which is capable of killing germs, bacteria and viruses. The composition also includes a minimal amount of alcohol, preferably anhydrous isopropyl alcohol or anhydrous ethyl alcohol or alternatively a minimal amount of water for dissolution of the QUAT and Triclosan, as well as one or more essential oils, anti-oxidants, a suitable aerosol propellant, and optionally fragrance.

Thus, an aspect of the present invention is that more than one germicide may be combined for an additive effect in killing germs and bacteria. The germicide components may be used in total (combined) amounts that range from about 0.5 to about 3 percent by weight of the sanitizing composition.

Thus, a single or blended germicide component with known persistent activity is used in the composition and delivered as an aerosol for the various embodiments of the present invention. Most conventional hand sanitizers contain only one germ killing agent, typically isopropyl alcohol or commercial grade ethyl alcohol, have non-persistent activity, and are generally delivered as gels or foams.

Other features of using an aerosolized persistent germicide containing one or more QUATS as the bioactive ingredient are its effectiveness as a hard surface sanitizer and disinfectant.

Another aspect and component is an emollient and skin conditioner, such as but not limited to the essential oils such as Sweet Almond Oil, Jojoba Oil, Shea Oil, Thyme Oil, Tea Tree Oil and Olive Oil. These essential oils work by protecting the skin, and increasing the ability of the skin to hold water, providing the skin with a layer of oil to prevent water loss, and thus lubricating the skin. This component may be used in amounts that range from 4.00 to about 6.00 percent of total weight.

Optional components may include fragrance, vitamins, proteins, amino acids, anti-oxidants, anti-aging agents, and the like. Fragrances may confer an odorous bouquet of fruit, tea, flowers, or other fresh odor upon use of the skin sanitizer. Included are oils of rosemary, peppermint, clove, cinnamon, rose, jasmine, lavender, germanium, almond (marzipan), anise, berry, banana, cherry and aloe Vera. Alternatively, the sanitizer may also be formulated without fragrance for individuals who do not desire or cannot tolerate fragrances. The fragrance, when added, is generally in amounts of about 0.25 to about 1.00 percent in weight. Optionally, stabilizing components such as vitamin E, or other anti-oxidative agents and/or preservatives such as ascorbic acid, citric acid and other similar compounds that are also antioxidants, as well as butylated hydroxyanisole (BHA) and butylated hydroxytoluene (BHT), paraben esters such as methyl or ethyl paraben which are preservatives may be mixed with the composition.

Cooling agents alone or combined with fragrance and essential oil may be incorporated into the composition. Included are such cooling agents as the many variations of menthol ketals and esters known as Frescolat (including but not limited to Frescolat x cool), menthol, camphor, eucalyptus, mint, peppermint and cornmint The aerosol embodiment of the sanitizer composition is directed to preparation of the composition and introducing it into a pressurize bearing container with a force activated valve for letting out the aerosol. The container may be constructed of metal such as aluminum, plastic or any other substance that is capable of providing a container that will hold pressure. Typical canister shapes and valves are those of a shaving crème can or a whipping cream can. The design and operation of such aerosol dispensers are known in the art.

The aerosolizing gas useful for providing the aerosol of the sanitizer composition includes one or more fluorochlorocarbon such as Freon, or another gas such as carbon dioxide, nitrous oxide and nitrogen. Although ordinary air can be used, anti-oxidants would be introduced to avoid oxidation of the components of the sanitizer composition by oxygen in the air. Methods for forming the aerosol in such a canister are known in the art.

The following are eight exemplary compositions in accordance with the present invention:

| Components | Weight Percent |
|---|---|
| Composition No. 1 | |
| Cyclomethicone | 93.67 |
| Sweet Almond Oil | 02.00 |
| Jojoba Oil | 02.00 |
| Fragrance | 01.00 |
| Benzalkonium chloride | 00.53 |
| Tocopheryl Acetate (Vitamin E) | 00.50 |
| Solvent* | 00.30 |
| | TOTAL 100% |
| Composition No. 2 | |
| Cyclomethicone | 93.47 |
| Sweet Almond Oil | 02.00 |
| Jojoba Oil | 02.00 |
| Fragrance | 01.00 |
| Benzalkonium chloride | 00.53 |
| Triclosan | 00.20 |
| Tocopheryl Acetate (Vitamin E) | 00.50 |
| Solvent* | 00.30 |
| | TOTAL 100% |
| Composition No. 3 | |
| Cyclomethicone | 93.67 |
| Sweet Almond Oil | 02.00 |
| Jojoba Oil | 02.00 |
| Fragrance | 01.00 |
| Benzalkonium chloride | 00.53 |
| Tocopheryl Acetate (Vitamin E) | 00.50 |
| Solvent* | 00.30 |
| | TOTAL 100% |
| Composition No. 4 | |
| Cyclomethicone | 93.47 |
| Sweet Almond Oil | 02.00 |
| Jojoba Oil | 02.00 |
| Fragrance | 01.00 |
| Benzalkonium chloride | 00.53 |
| Triclosan | 00.20 |
| Tocopheryl Acetate (Vitamin E) | 00.50 |
| Solvent* | 00.30 |
| | TOTAL 100% |

-continued

| Components | Weight Percent |
|---|---|
| Composition No. 5 | |
| Cyclomethicone | 93.67 |
| Sweet Almond Oil | 02.00 |
| Shea Oil | 02.00 |
| Fragrance | 01.00 |
| Benzalkonium chloride | 0.13-00.53 |
| Tocopheryl Acetate (Vitamin E) | 00.50 |
| Solvent* | QED |
| TOTAL | 100% |
| Composition No. 6 | |
| Cyclomethicone | 93.47 |
| Sweet Almond Oil | 02.00 |
| Shea Oil | 02.00 |
| Fragrance | 01.00 |
| Benzalkonium chloride | 0.13-00.53 |
| Triclosan | 00.20 |
| Tocopheryl Acetate (Vitamin E) | 00.50 |
| Solvent* | QED |
| TOTAL | 100% |
| Composition No. 7 | |
| Cyclomethicone | 93.67 |
| Sweet Almond Oil | 02.00 |
| Shea Oil | 02.00 |
| Fragrance | 01.00 |
| Benzalkonium chloride | 0.13-00.53 |
| Tocopheryl Acetate (Vitamin E) | 00.50 |
| Solvent* | QED |
| TOTAL | 100% |
| Composition No. 8 | |
| Cyclomethicone | 93.47 |
| Sweet Almond Oil | 02.00 |
| Jojoba Oil | 02.00 |
| Fragrance | 01.00 |
| Benzalkonium chloride | 0.13-00.53 |
| Triclosan | 00.20 |
| Tocopheryl Acetate (Vitamin E) | 00.50 |
| Solvent* | QED |
| TOTAL | 100% |

*The solvent may be cyclomethicone, water, or an alcohol such as ethanol or isopropanol. Preferably, the solvent is alcohol, more preferably the solvent is water; most preferably the solvent is cyclomethicone so that the composition is completely free of water and alcohol.

In one embodiment of the present invention and as seen in Compositions 1 and 5 above, the formula contains Cyclomethicone at 93.67%, Sweet Almond Oil at 2.00%, Jojoba Oil of Shea Oil at 2.00%, Benzalkonium chloride at 0.53%, Tocopheryl Acetate (Vitamin E) at 0.50%, Solvent* at 0.30%, and optional fragrance at 1.00%.

In one embodiment of the present invention and as seen in Compositions 2 and 6 above, the formula contains Cyclomethicone at 93.67%, Sweet Almond Oil at 2.00%, Jojoba Oil or Shea Oil at 2.00%, Benzalkonium chloride at 0.53%, Triclosan at 0.20%, Tocopheryl Acetate (Vitamin E) at 0.50%, Solvent* at 0.30%, and optional fragrance at 1.00%.

In one embodiment of the present invention and as seen in Compositions 3 and 7 above, the formula contains Cyclomethicone at 93.67%, Sweet Almond Oil at 2.00%, Jojoba Oil or Shea Oil at 2.00%, Benzalkonium chloride at 0.53%, Tocopheryl Acetate (Vitamin E) at 0.50%, Solvent* at 0.30%, and optional fragrance at 1.00%.

In one embodiment of the present invention and as seen in Compositions 4 and 8 above, the formula contains Cyclomethicone at 93.67%, Sweet Almond Oil at 2.00%, Jojoba Oil or Shea Oil at 2.00%, Benzalkonium chloride at 0.53%, Triclosan at 0.20%, Tocopheryl Acetate (Vitamin E) at 0.50%, solvent* at 0.30%, and optional fragrance at 1.00%.

*See the description above for the listing of Solvent and its preferred forms.

In one embodiment of the present invention the formularist combines one or more of the bioactive ingredient and solvent together creating a base API mixture. The essential oils, tocopheryl acetate, and fragrance are then added together to the base API mixture. As a final step, the cyclomethicone is added to complete the composition and mixed. Then preferably filled into aerosol compatible containers or alternatively into pump sprayers as desired, The advantage of this method is to create a precise blending process of the ingredients that provide uniform distribution of ingredients and prevent an emulsion or separation.

In one embodiment of the present invention, a 2-3 second continuous spray from a distance of 5-6 inches is sufficient to effectively apply a sufficient amount to disinfect both hands front and back. In one embodiment of the present invention the formula dries quickly, does not leave the hands feeling tight, sticky or excessively dry.

The composition may be applied to the hands or skin generally in a variety of forms, such as a liquid, aerosol, foam and gel positioned within a variety of containers. It is envisioned that the various embodiments of the present invention can be packaged in various ways such as but not limited to valve pump bottles, aerosol containers, and squirt bottles of varying size, disposable towelettes, whether individually packaged or packaged in bulk, touch-free dispensers, or combinations thereof.

When the composition is configured as an aerosolizable sanitizer, it is contained in a pressurized canister. This article comprises a pressurizable canister with a manually operable discharge valve. The canister contains an aerosolizing gas selected from the group consisting of a fluorocarbon, a fluorochlorocarbon, nitrogen, nitrous oxide, carbon dioxide and any combination thereof and a sanitizer composition described above wherein the aerosolizing gas and composition are present in concentrations effective to provide an aerosolized sanitizer composition upon their release from the pressurizable canister. The article for the aerosolizable sanitizer may be configured so that the composition and aerosolizing gas are not separated by a barrier and released by a manually operated valve or manual dose metered valve. Alternatively, the article for the aerosolizable sanitizer may be configured so that the composition and aerosolizing gas are separated by a barrier bag on valve configuration, and released by a manually operated valve or manual dose metered valve.

Alternatively, the sanitizer composition may be applied using a spray bottle. The spray bottle includes a container with a pump actuator capable of delivering a stream, spray or foam of a substance contained within the container, the substance being a sanitizer composition.

In another alternative, the sanitizer composition may be applied using a squeeze bottle. The plastic squeeze bottle has a narrow mouth or small orifice for dispensing the sanitizing composition contained within the bottle.

This invention has been described in detail with particular references to certain embodiments. The above examples and embodiments should be considered to be illustrative and no way limiting of the present invention. Thus, while the description above refers to particular examples, and embodiments, it will be understood that many modifications may be made without departing from the spirit thereof.

What is claimed is:

1. A sanitizer composition suitable for use on human skin, comprising:
   (a) from about 89% to about 97% cyclomethicone;
   (b) from about 2.00% to about 4.00% Sweet Almond Oil;
   (c) from about 2.00% to about 4.00% Jojoba Oil or Shea Oil;
   (d) from about 0.25% to about 0.75% tocopheryl acetate;
   (e) from about 0.13% to about 0.53% quaternary ammonium salt having germicidal activity;
   (f) from about 0.30% to about 1.00% solvent; and
   (g) from about 0.25% to about 1.00% fragrance.

2. The sanitizer composition of claim 1, wherein the quaternary ammonium salt is selected from the group consisting of benzalkonium chloride, benzethonium chloride, methylbenzethonium chloride, cetalkonium chloride, cetylpyridinium chloride, cetrimonium chloride, cetrimide, dofanium chloride, tetraethylammonium bromide, domiphen bromide and any combination thereof.

3. The sanitizer composition of claim 1, wherein the solvent is additional cyclomethicone, water, ethanol or isopropanol.

4. The sanitizer composition of claim 3, wherein the solvent is essentially anhydrous.

5. The sanitizer composition of claim 1, further comprising one or more additives selected from the group consisting of additional essential oils, vitamins, proteins, amino acids, antioxidants and stabilizers/preservatives.

6. The sanitizer composition of claim 1, further comprising Triclosan as a second germicide.

7. The sanitizer composition of claim 1, wherein the solvent is additional cyclomethicone, alcohol or water.

8. The sanitizer composition of claim 1, wherein the solvent is anhydrous ethyl alcohol or isopropyl alcohol or water.

9. The sanitizer composition of claim 1, wherein the quaternary ammonium salt is selected from the group consisting of benzalkonium chloride, benzethonium chloride, methylbenzethonium chloride, cetalkonium chloride, cetylpyridinium chloride, cetrimonium chloride, cetrimide, dofanium chloride, tetraethylammonium bromide, domiphen bromide and any combination thereof.

10. A hand sanitizing composition comprising, by Weight:
    (a) from about 89% to about 97% cyclomethicone;
    (b) from about 2.00% to about 4.00% Sweet Almond Oil;
    (c) from about 2.00% to about 4.00% Jojoba Oil or Shea Oil;
    (d) from about 0.25% to about 0.75% tocopheryl acetate;
    (e) from about 0.13% to about 0.53% quaternary ammonium salt;
    (f) from about 0.10% to about 0.20% Triclosan;
    (g) from about 0.30% to about 1.00% solvent; and
    (h) from about 0.25% to about 1.00% fragrance.

11. The composition of claim 10, wherein the solvent is additional cyclomethicone, alcohol or water.

12. The composition of claim 10, wherein the solvent is anhydrous ethyl alcohol or isopropyl alcohol or water.

13. The composition of claim 10, wherein the quaternary ammonium salt is selected from the group consisting of benzalkonium chloride, benzethonium chloride, methylbenzethonium chloride, cetalkonium chloride, cetylpyridinium chloride, cetrimonium chloride, cetrimide, dofanium chloride, tetraethylammonium bromide, domiphen bromide and any combination thereof.

14. An article comprising a pressurizable canister with a manually operable discharge valve, the canister containing an aerosolizing gas selected from the group consisting of a fluorocarbon, a fluorochlorocarbon, nitrogen, nitrous oxide, carbon dioxide and any combination thereof and a sanitizer composition wherein the aerosolizing gas and composition are present in concentrations effective to provide an aerosolized sanitizer composition upon their release from the pressurizable canister, the sanitizer composition comprising:
    (a) from about 89% to about 97% cyclomethicone;
    (b) from about 2.00% to about 4.00% Sweet Almond Oil;
    (c) from about 2.00% to about 4.00% Jojoba Oil or Shea Oil;
    (d) from about 0.25% to about 0.75% tocopheryl acetate;
    (e) from about 0.13% to about 0.53% quaternary ammonium salt having germicidal activity;
    (f) from about 0.30% to about 1.00% solvent and
    (g) from about 0.25% to about 1.00% fragrance.

15. The aerosolizable sanitizer of claim 14, wherein the composition and aerosolizing gas are not separated by a barrier and released by a manually operated valve or manual dose metered valve.

16. The aerosolizable sanitizer of claim 14, wherein the composition and aerosolizing gas are separated by a barrier bag on valve configuration, and released by a manually operated valve or manual dose metered valve.

17. The sanitizer composition of claim 1, wherein the composition is delivered in a spray sanitizer comprising a container with a pump actuator capable of delivering a stream, spray or foam of the sanitizer composition.

18. The sanitizer composition of claim 1, wherein the sanitizer composition is prepared by at least:
    (a) combining solvent and a quaternary ammonium salt to form a base mixture;
    (b) adding essential oils, preservative/stabilizer and optional fragrance to the base mixture to form a second mixture;
    (c) then adding cyclomethicone to the second mixture to prepare the sanitizer composition of claim 1.

19. The sanitizer composition of claim 2, wherein the quaternary ammonium salt is benzalkonium chloride.

20. The sanitizer composition of claim 9, wherein the quaternary ammonium salt is benzalkonium chloride.

21. The sanitizer composition of claim 13, wherein the quaternary ammonium salt is benzalkonium chloride.

22. The article of claim 14 comprising a plastic squeeze bottle with a narrow mouth for dispensing a sanitizing composition contained within the bottle.

23. The composition of claim 1, wherein the solvent is cyclomethicone and the composition is completely alcohol and water free.

24. The composition of claim 10, wherein the solvent is cyclomethicone and the composition is completely alcohol and water free.

25. The composition of claim 1, wherein the solvent is water and the composition is completely alcohol free.

* * * * *